United States Patent [19]

Anshus et al.

[11] 4,139,696

[45] Feb. 13, 1979

[54] CONTINUOUS POLYMERIZATION OF 2-PYRROLIDONE

[75] Inventors: Byron E. Anshus, Orinda; Kiyoshi Katsumoto, El Cerrito; Ira M. Serkes, Berkeley, all of Calif.

[73] Assignee: Chevron Research Company, San Francisco, Calif.

[21] Appl. No.: 792,421

[22] Filed: Apr. 29, 1977

[51] Int. Cl.² .......................................... C08G 69/24
[52] U.S. Cl. ................................... 528/312; 528/315; 528/326
[58] Field of Search ............................. 260/78 P, 78 L

[56] References Cited

U.S. PATENT DOCUMENTS

| | | | |
|---|---|---|---|
| 3,184,476 | 5/1965 | Wingfield et al. | 260/78 P |
| 3,213,066 | 10/1965 | Renfrew | 260/78 P |
| 3,681,293 | 8/1972 | Jarovitzky et al. | 260/78 P |
| 3,778,402 | 12/1973 | Kimura et al. | 260/78 P |

*Primary Examiner*—Harold D. Anderson
*Attorney, Agent, or Firm*—D. A. Newell; T. G. DeJonghe; Lawrence S. Squires

[57] ABSTRACT

2-Pyrrolidone is continuously polymerized to a high-molecular-weight particulate product by the stirred polymerization of the carbonated alkaline polymerizate. The polymerizate is prepared by contacting an aqueous hydroxide with excess 2-pyrrolidone, maintaining the resultant alkaline mixture at an elevated temperature for sufficient time to reduce the 2-pyrrolidone dimer content of the mixture to within the desired limits, dehydrating the alkaline mixture to reduce the water content to within the desired limits, and contacting the alkaline mixture with carbon dioxide to form the carbonated alkaline polymerizate. The paste of particular polypyrrolidone and liquid polymerizate is continuously withdrawn from the reactor, neutralized with aqueous acid and washed with warm water.

10 Claims, 1 Drawing Figure

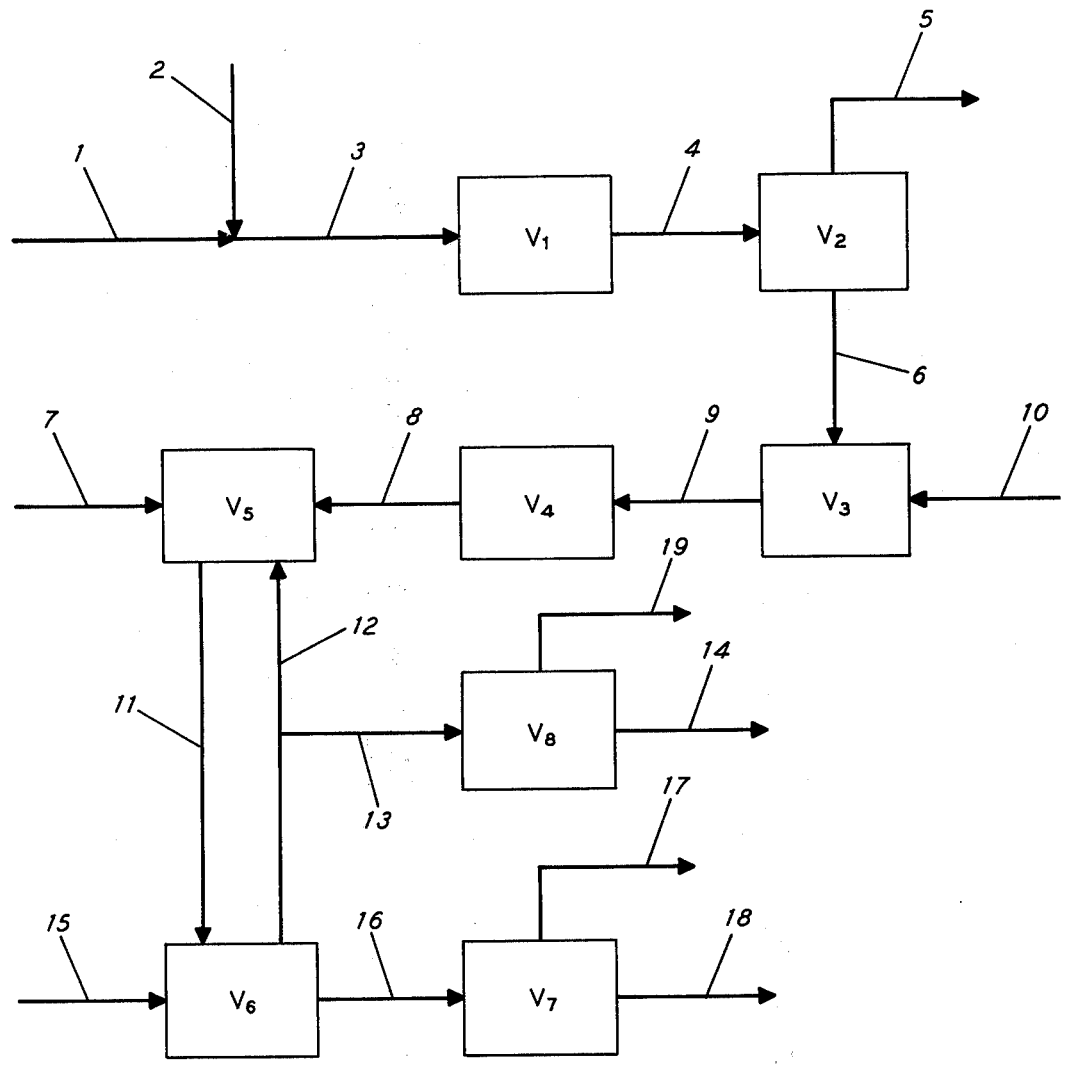

This invention relates to a continuous process for the production of poly-2-pyrrolidone by the in situ production of catalysts for the polymerization of 2-pyrrolidone, polymerization under agitation and the isolation of the particulate polypyrrolidone product. Poly-2-pyrrolidone is produced by the alkaline catalyzed polymerization of 2-pyrrolidone. The catalyzed polymerization is initiated by a "dimer" formed by the condensation of two 2-pyrrolidone molecules or by other initiators such as N-acyl pyrrolidone. The dimer is systematically designated 1-(1-pyrrolin-2-yl)-2-pyrrolidinone. It is more conveniently called pyrrolinyl-pyrrolidone, or "dimer". Dimer is present in commercially available 2-pyrrolidone in greater or lesser amounts. It is removed by fractional distillation with great difficulty or not at all.

Polypyrrolidone has heretofore been produced by batch bulk polymerization. The monomer and catalysts were charged to a reactor and held at polymerization temperature for 20 or more hours to obtain a hard block of polymer. Since, in general, only 30–70 percent of the monomer was converted to polymer, the product had to be chopped, ground and extracted with water to recover unreacted monomer. The final polymer particle size depended on the extent of grinding, as well as the percent conversion to polymer. Polymerization under agitation, such as in a stirred reactor, produces a product which is a powder or alkaline paste or slurry of particulate polypyrrolidone and polymerizate. At conversions above about 40 percent, the product is powdery. The product is conveniently washed with water to provide a particulate polypyrrolidone without grinding. However, a considerable amount of polymer degradation occurs if the alkaline product is contacted with water while still at the elevated temperature of the polymerization reactor. If, on the other hand, the alkaline product is allowed to cool before contacting with water, it becomes a hard block of polymer requiring the same processing as the batch bulk polymerization product.

2. Prior Art

In U.S. Pat. No. 3,184,476 pyrrolinyl-pyrrolidone is removed from 2-pyrrolidone by heating with water for several hours at a temperature greater than 80° C. Slight acidification of the 2-pyrrolidone was found to accelerate the hydrolysis of the dimer. On the other hand, alkaline hydrolysis of the sensitive 2-pyrrolidone ring is said to occur even under mild conditions of prolonged heating of aqueous alkaline 2-pyrrolidone (see U.S. Pat. Nos. 3,778,402 and 3,681,293). U.S. Pat. No. 3,213,066 discloses the production of granular polypyrrolidone by polymerization in a ball mill reactor. In the continuous polymerization process of U.S. Pat. No. 3,681,293 the polymerizate is extruded, and pelletized before drying and washing.

SUMMARY OF THE INVENTION

A process for the polymerization of 2-pyrrolidone by contacting an aqueous hydroxide solution with excess 2-pyrrolidone to form an aqueous alkaline mixture wherein the aqueous alkaline mixture is maintained at an elevated temperature for the period of time necessary to reduce the dimer content of the mixture to within the desired limits for optimum rate of polymerization and product molecular weight, by hydrolysis of the dimer. The alkaline mixture is dehydrated to reduce its water content to less than about 1000 ppm and is contacted with carbon dioxide to produce the polymerizate, a carbonated alkaline mixture. The polymerizate is maintained at a temperature of about 20°–90° C. under agitation in a polymerization zone which comprises one or more polymerization reactors to produce a product which is a powder, paste or slurry of particulate poly-2-pyrrolidone in the polymerizate. The product is withdrawn from the polymerization zone at polymerization temperature and is contacted with aqueous acid solution to produce an aqueous slurry having a pH of about 5–8. The aqueous slurry is then washed with water to obtain the particulate poly-2-pyrrolidone product.

DESCRIPTION OF PREFERRED EMBODIMENTS

In the present process for the polymerization of 2-pyrrolidone, and specifically in the continuous production of catalysts for this polymerization, an aqueous hydroxide, such as 40% by weight aqueous potassium hydroxide, is mixed with an excess of distilled monomer to form an alkaline mixture which is subjected to a rapid dehydration. Rapid dehydration may be accomplished for example, by flash evaporation, such as in a thin-film evaporator. The dehydrated product is a substantially anhydrous solution of a pyrrolidonate salt, such as potassium 2-pyrrolidonate, in 2-pyrrolidone. The 2-pyrrolidonate salt is a polymerization catalyst. This solution is then sent to a carbonator, or the polymerization vessel, where carbon dioxide is added to the solution to form a carbonated alkaline mixture which is then held under polymerization conditions. Rapid dehydration of the alkaline mixture was favored to avoid the base-catalyzed hydrolysis of 2-pyrrolidone to 4-aminobutyric acid which interfered with carbonation and thereby reduced the amount of carbonated catalysts available. If carbonation is substantially affected, then the yield of high molecular weight poly-2-pyrrolidone is greatly reduced. We discovered that dimer was destroyed (hydrolyzed) by heating in the presence of base. Less dimer is destroyed by rapid dehydration than by longer dehydration. In the polymerization of 2-pyrrolidone it is found necessary to balance the need to hydrolyze pyrrolinyl-pyrrolidone (dimer) against the danger of hydrolyzing the sensitive 2-pyrrolidone ring.

In order to achieve the high conversion of 2-pyrrolidone to polymer of high molecular weight, it is desireable to maintain a close control of the nature and amount of polymerization initiators and polymerization catalysts present in the polymerizate. Because each molecule of initiator is theoretically capable of giving rise to one polymer molecule, it is hypothesized that an overabundance of initiator molecules produces a high conversion of monomer to polymer of low molecular weight in a short time. This is evidenced in a continuous polymerization process by line plugging or build-up of low-molecular-weight solid polypyrrolidone. For example, the presence of 0.6 weight percent of pyrrolinyl-pyrrolidone in the monomer feed was found to produce excessive line plugging by premature polymerization. This problem is not encountered when catalyst is prepared by batch dehydration of the pyrrolidone-KOH solution because the longer dehydration time required in batch polymerization destroyed in pyrrolinyl-pyrrolidone polymerization initiator. The continuous process, with its short contact time between the addition of aqueous hydroxide and the charging of the polymerizate to the reactor was found to present the unexpected risk of a runaway polymerization because the amount of dimer was not sufficiently reduced. On the other hand, the optimum selection of the amount of a selected initiator produces a high conversion of monomer to polymer of high molecular weight in a reasonable period of time. It is found that such an initiated continuous polymerization can be achieved by optimization of the amount of pyrrolinyl-pyrrolidone in the polymerizate by continuously subjecting the alkaline mixture of aqueous hydroxide and 2-pyrrolidone to a brief heat treatment, i.e., a step achieving hydrolysis of the dimer.

In preferred embodiments of this invention 2-pyrrolidone is purified for polymerization by fractional distillation. The middle fraction is taken, but it may contain as much as several percent pyrrolidnyl-pyrrolidone, typically about 1 weight percent pyrrolinyl-pyrrolidone. This amount of dimer is both exceedingly difficult to remove and very deleterious to the continuous polymerization process.

The middle fraction of 2-pyrrolidone is used for in situ catalyst production by contacting same with an aqueous hydroxide solution. The aqueous hydroxide solution may be a solution of an alkaline metal hydroxide, an alkaline earth metal hydroxide, or a quaternary ammonium hydroxide. Preferably, it is an alkali metal hydroxide such as aqueous NaOH or preferably aqueous KOH, having a concentration of 10–60 weight percent hydroxide. An aqueous NaOH solution of about 10–25 weight percent NaOH is also preferred, but most satisfactory results have heretofore been obtained with aqueous KOH solutions of 20–60 weight percent, and usually of 35–45 weight percent KOH. (See U.S. Pat. No. 3,778,402). The aqueous hydroxide is continuously contacted with the distilled 2-pyrrolidone in relative amounts such that an excess of 2-pyrrolidone is present. The hydroxide and 2-pyrrolidone are normally fed at a rate such that hydroxide constitutes 0.5–30 mol percent, preferably about 5–20 mol percent, and most preferably about 10 mol percent of the mixture, based on total 2-pyrrolidone. That is, after dehydration, the amount of catalysts, i.e. the amount of 2-pyrrolidonate salts, constitutes 0.5–30 mol percent, preferably about 5–20 mol percent, and most preferably about 10 mol percent of the dehydrated mixture based on total 2-pyrrolidone. Total 2-pyrrolidone includes both 2-pyrrolidone and 2-pyrrolidonate salt.

In order to reduce the dimer content of the alkaline mixture within the desired limits by hydrolysis of the dimer, the alkaline mixture of aqueous hydroxide and 2-pyrrolidone is maintained at a temperature of about 25°–60° C., preferably 30°–50° C., for a period of about 3–60 minutes, preferably about 10–20 minutes, at a pressure ranging from subatmospheric to superatmospheric, preferably at atmospheric pressure. It is understood that the time period of hydrolysis which is selected may be varied inversely to the temperature of hydrolysis which is selected, and vice versa, to achieve hydrolysis of the dimer to within the desired limits. The hydrolysis zone may simply consist of an isolated and thermostated vessel whose volume is chosen to give a residence time corresponding to the selected period of hydrolysis under the chosen conditions of continuous feeding of the alkaline mixture and temperature. Depending on the dimer content of the distilled monomer, the alkaline mixture may enter the hydrolysis zone containing appreciable pyrrolinyl-pyrrolidone, but it exits from this zone after the selected period of hydrolysis containing about 0.01–0.1 weight percent dimer and preferably containing less than 0.05 weight percent dimer, based on the weight of total 2-pyrrolidone, (the weight of total 2-pyrrolidone includes the weight of 2-pyrrolidone and its salt).

The alkaline mixture, containing only the desired amount of dimer, is sent to the dehydration zone consisting, for example, of a thin-film evaporator, or a vacuum distillation column, where water is rapidly removed under conditions which provide a dehydrated mixture containing less than about 1000 ppm water, preferably less than 500 ppm water, based on the weight of total 2-pyrrolidone. Preferably the mixture is dehydrated under reduced pressure, preferably at 2–100 mm, and most preferably at 2–10 mm and about 75°–190° C. The dehydrated alkaline mixture of 2-pyrrolidonate salt and 2-pyrrolidone is then sent to the carbonation zone, preferably being transferred through heated lines which maintain a temperature of about 70–90° C. in order to retard polymerization. To the substantially anhydrous mixture containing less than about 1000 ppm water, is added carbon dioxide, preferably while said dehydrated alkaline mixture is maintained at a temperature of about 60°–95° C., preferably 70°–90° C. Sufficient carbon dioxide is absorbed by the alkaline mixture by provision of contact area and contact time such that carbon dioxide is added to the extent of about 10–50 mol percent based on the hydroxide, thus at 10 mol percent hydroxide, carbon dioxide is added to the extent of about 1–5 mol percent based on total 2-pyrrolidone. Preferably, carbon dioxide constitutes about 1–5 mol percent, most preferably about 3 mol percent of the alkaline mixture based on total 2-pyrrolidone. The carbonated alkaline mixture is sent to the polymerization zone where it is preferably mixed with additional purified monomer and additional polymerization promoters such as N-acyl compounds, tetramethylammonium halide, sulfur dioxide, acetic acid anhydride, dimer, etc.

Dimer, present in the purified monomer in known amount, is conveniently added to the polymerizate in controlled amounts by this means to initiate polymeriation. Preferably, about 0.08–0.15 weight percent dimer, based on total 2-pyrrolidone including the added monomer, is added to the polymerizate by means of the addition of purified monomer.

The polymerization zone consists of one or more reactors, preferably used in series, wherein the temperature is maintained at 20–90° C., preferably about 40–60° C. and most preferably about 45–55° C., and wherein the polymerizate is subjected to continual agitation, such as is provided by a stirred reactor mechanism. In continuous operation, the number of pounds of polymerizate in the reactor, divided by the feed rate of polymerizate in pounds/hour (which is substantially identical to the product take-off rate in continuous operation) equals the residence time in the polymerization reactor. The residence time, i.e. the reactor volume and the feed rate, is selected to provide product polymer of the desired molecular weight and to provide the desired degree of conversion of monomer to polymer. Generally, residence times are 4–36 hours, preferably 6–24 hours, depending on the temperature, the product desired, and the amounts of initiator and catalysts used to achieve that product.

The polymer exits the polymerization zone and is subjected to washing, drying, pelletization, etc. as may be necessary for its ultimate use. Under these continuous polymerization conditions, the agitated reactor holds a product which is a powder, paste or slurry consisting of particulate poly-2-pyrrolidone in the polymerizate, i.e. in the carbonated alkaline mixture continuously provided. Preferably, the reactor holds a viscous paste which is withdrawn from the polymerization zone by an auger-like, or screw-like take-off at a constant continuous rate. In another preferred embodiment, the product is continuously taken as an overflow discharge from the reactor. While maintaining the product at about polymerization zone temperature, or before substantial cooling of the product to a hard mass is allowed to occur, it is contacted with an aqueous acid solution to form an aqueous slurry having a pH of about 5-8. Preferably the contact is made in a neutralizer with mixing. Preferably a strong mineral acid solution such as a sulfuric acid solution is used for neutralization. Mixing the product with acid solution to provide a substantially neutral slurry inhibits further reaction, prevents polymer agglomeration, prevents basecatalyzed polymer degradation by hydrolysis, and consequently permits washing with water at higher temperature. The aqueous slurry is washed with water, preferably at an elevated temperature of no higher than about 70°-80° C., to obtain the particulate polypyrrolidone product. Preferably the slurry is pumped from the neutralizer to a countercurrent washer.

The process of the present invention is just as applicable to the production of polymers of C-alkyl-substituted pyrrolidone, such as 4-methyl-2-pyrrolidone, and the production of copolymers of 2-pyrrolidone, such as pyrrolidone/caprolactam copolymers as to the production of poly-2-pyrrolidone. Consequently, in general, and unless otherwise indicated, this process will find use in the polymerization of 2-pyrrolidone, substituted 2-pyrrolidone, and any monomer capable of copolymerizing with 2-pyrrolidone under the stated conditions of alkaline polymerization catalysis. Preparation of polymers of 2-pyrrolidone using the process of this invention can be carried out with various amounts of monomer, catalysts, inert non-solvent liquids as in a dispersion polymerization, initiators, activators and other additives — the amount of each being properly coordinated to produce the most effective polymerization. Although the preferred amounts of the components have been given, it is to be understood that these are not intended to be limitations to polymerization, since it may be possible to affect substantial polymerization outside the preferred ranges. Such polymerization initiators and catalysis aids include N-acyl lactams such as N-acetyl pyrrolidone or equivalently compounds such as acetic anhydride. Sulfur dioxide may be usable as a partial substitute for carbon dioxide and tetraalkyl ammonium halides such as tetramethyl ammonium chloride may find use in the polymerizate.

The accompanying diagram illustrates an embodiment of the process of the present invention. Referring to the drawing, 2-pyrrolidone is admitted through line 1 and is joined with aqueous potassium hydroxide solution admitted through line 2. After the mixing of 2-pyrrolidone and aqueous potassium hydroxide, as in a line mixer in line 3, the alkaline mixture enters $V_1$, a heated vessel, wherein the aqueous alkaline mixture is maintained at 25°-60° C. for an average residence time of about 5-60 minutes. The aqueous alkaline mixture next passes via line 4 to $V_2$, the dehydration zone, wherein a wiped-film evaporator removes water via line 5 and passes the dehydrated alkaline mixture via line 6 to the carbonator $V_3$ wherein carbon dioxide is added through line 10. (Preferably, the dehydrated alkaline mixture passes directly from $V_2$ to the polymerization zone $V_4$ wherein a constant carbon dioxide pressure is maintained over the polymerizate.) The carbonated alkaline mixture is maintained at about 70°-90° C. while passing in line 9 from $V_3$ to the polymerization zone $V_4$ wherein it is maintained at polymerization temperature in a continuously stirred reactor for an average residence time of about 4-36 hours. The product, having the consistency of a powder, paste or slurry, is removed from $V_4$ by either an auger or by overflow and is then fed to the neutralizer $V_5$ via line 8. Concentrated sulfuric acid is concurrently added to the neutralizer via line 7. The neutralized aqueous slurry formed in $V_5$ is fed via line 11 to a countercurrent washer $V_6$ concurrently with water from line 15. The used wash water from $V_6$ containing unpolymerized 2-pyrrolidone, as well as $K_2SO_4$, is sent via line 13 to the monomer recovery zone $V_8$, but a fraction of the used wash water passes via line 12 to neutralizer $V_5$ wherein it is mixed with the concurrently provided acid and product to form the aqueous slurry. Recovered 2-pyrrolidone exits the monomer recovery zone $V_8$ via line 14 while water is removed through line 19. Recovered monomer may be recycled through line 1 or taken-off for further purification. Washed polymer proceeds via line 16 to the dryer $V_7$ from which water leaves via line 17 and dry polypyrrolidone is obtained from line 18. The polymer, so dried, may be obtained with some residual moisture. The moisture content of this stage depends on further processing conditions and requirements, but should preferably be less than about 40-25 weight percent water, most preferably less than 25 weight percent water. When further processing includes melt extrusion pelletization, at that stage, the water content should be reduced below about 0.1 weight percent water.

EXEMPLIFICATION

EXAMPLE 1

2-Pyrrolidone was contacted with a 40 weight percent KOH aqueous solution in a feed line at 35° C. for 3 minutes prior to flash evaporation of a water in a thin-film evaporator. The resulting dehydrated alkaline mixture was carbonated and allowed to polymerize to 50% conversion at about 50° C. The polymer weight average molecular weight was found to be about 190,000. In comparative runs under otherwise identical conditions, the alkaline mixture was held at 55° C. for 3 minutes prior to flash evaporation to give a polymer product having a molecular weight of about 260,000. In another comparative run under identical conditions, the alkaline mixture was held at 38° C. for 20 minutes prior to flash evaporation and the polymer product had a molecular weight of about 230,000.

The following calculated example is based upon continuous processes actually carried out separately on various steps of the overall process.

EXAMPLE 2

Two thousand pounds/hr of freshly distilled 2-pyrrolidone is charged through a line mixer simultaneously with 330 pounds/hr of a 40% aqueous potassium hydroxide solution. The alkaline mixture is then transferred at 2330 pounds/hr to a vessel maintained at 40° C. After an average residence time of 15 minutes, the heat-treated alkaline mixture is passed into a distillation zone comprising a wiped-film evaporator maintained at 80° C. and 3 mm pressure, and wherein 240 pounds/hr of water is vaporized and removed from the alkaline mixture. The dehydrated alkaline mixture at 80° C. is next passed at 2121 pounds/hr into a carbonation vessel wherein it reacts with 31 pounds/hr of carbon dioxide. The resultant carbonated alkaline mixture is maintained at 80° C. while passing from the carbonation vessel to the polymerization reactor. The polymerization reactor is a stirred, conical vessel in which about 16,000 pounds of polymerizate is continuously mixed at 50° C. The polymerization vessel contains a heavy paste of particulate polypyrrolidone and liquid polymerizate which is removed by means of an auger, and with essentially no cooling is charged to the neutralization vessel at 2121 pounds/hr after an average polymerization time of 6–8 hours. The neutralizer is concurrently provided with 120 pounds/hr of concentrated sulfuric acid and 1000 pounds/hr of a water-pyrrolidone-$K_2SO_4$ solution from the countercurrent washer. The resulting slurry is stirred at a temperature of 50° C. for an average of 10 minutes. Overflow from the neutralizer next passes at 3241 pounds/hr into a water washer wherein it is contacted countercurrently by 5000 pounds/hr of water at 50° C. The used wash water, containing 1000 pounds/hr of pyrrolidone, is sent to monomer recovery facilities. The washed polymer, 1500 pounds/hr, is dried by heating at 120° C. under atmospheric pressure in a fluidized dryer for 30 minutes. In this way, there is obtained 1000 pounds/hr of dry, polypyrrolidone powder having a weight average molecular weight of about 200,000.

What is claimed is:

1. A continuous process for the polymerization of 2-pyrrolidone comprising
    (a) contacting an aqueous alkaline hydroxide solution with excess 2-pyrrolidone, containing more than about 0.1 weight percent dimer, to form an aqueous alkaline mixture,
    (b) maintaining said aqueous alkaline mixture at an elevated temperature in the range of about from 25–60° C. for a period of time necessary to reduce the dimer content of said mixture to about from 0.01 to 0.1 wt %, based on the weight of total pyrrolidone,
    (c) rapidly dehydrating said aqueous alkaline mixture to reduce its water content to less than about 1000 ppm,
    (d) contacting the dehydrated alkaline mixture with carbon dioxide to produce a carbonated alkaline mixture,
    (e) maintaining said carbonated alkaline mixture under agitation in a polymerization zone at a polymerization temperature to form a product comprising particulate poly-2-pyrrolidone in said carbonated alkaline mixture,
    (f) withdrawing said product from said polymerization zone, and
    (g) washing said aqueous slurry with water to obtain a particulate poly-2-pyrrolidone product.

2. The process for the polymerization of 2-pyrrolidone according to claim 1, wherein said aqueous alkaline hydroxide solution is an aqueous alkali metal hydroxide solution.

3. The process for the polymerization of 2-pyrrolidone according to claim 2, wherein said alkali metal hydroxide solution is a potassium hydroxide solution containing 20–60 weight percent KOH.

4. The process for the polymerization of 2-pyrrolidone according to claim 1, wherein said alkaline mixture is dehydrated under reduced pressure to reduce the water content to less than about 500 ppm.

5. The process for the polymerization of 2-pyrrolidone according to claim 1, wherein said dehydrated alkaline mixture is maintained at and is contacted with carbon dioxide at a temperature of about 60–95° C. to provide a carbonated alkaline mixture containing about 1–5 mol percent carbon dioxide based on total 2-pyrrolidone and said polymerization temperature is 40°–60° C.

6. The process for the polymerization of 2-pyrrolidone according to claim 1, wherein said polymerization zone comprises one or more stirred reactors in series and said polymerization temperature is 40–60° C.

7. The process of claim 1 wherein said aqueous alkaline mixture is maintained at an elevated temperature in the range of about from 30–50° C.

8. The process of claim 1 wherein said aqueous alkaline mixture is maintained at said elevated temperature for a period of time necessary to reduce the dimer content of said mixture to less than 0.05 wt %, based on the weight of total pyrrolidone.

9. The process of claim 1 wherein said alkaline hydroxide is selected from the group consisting of alkali metal hydroxide, alkali earth metal hydroxide, and quaternary ammonium hydroxide.

10. The process of claim 1 wherein said aqueous alkaline mixture is maintained at said elevated temperature for about from 3 to 60 minutes.

* * * * *